(12) United States Patent
Boone et al.

(10) Patent No.: US 6,211,150 B1
(45) Date of Patent: Apr. 3, 2001

(54) ANALOGS OF CATIONIC PROTEINS

(75) Inventors: Thomas Charles Boone, Newbury Park; Ellen Ngoi Yin Cheung, Agoura; Susan Irene Hershenson, Newbury Park; John David Young, Thousand Oaks, all of CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/214,214

(22) PCT Filed: Jul. 17, 1997

(86) PCT No.: PCT/US97/12609

§ 371 Date: Dec. 23, 1998

§ 102(e) Date: Dec. 23, 1998

(87) PCT Pub. No.: WO98/03546

PCT Pub. Date: Jan. 29, 1998

Related U.S. Application Data

(63) Continuation-in-part of application No. 08/684,353, filed on Jul. 19, 1996, now abandoned.

(51) Int. Cl.[7] .................... A61K 38/00; C07H 21/02; C07H 21/04; C12P 21/06; C12N 1/20
(52) U.S. Cl. ................... 514/12; 536/23.1; 536/23.5; 530/402; 435/69.1; 435/70.1; 435/71.1; 435/252.3; 435/320.1
(58) Field of Search .................. 536/23.1, 23.5; 530/402; 514/12; 435/69.1, 70.1, 71.1, 252.3, 320.1

(56) References Cited

U.S. PATENT DOCUMENTS 5,322,678   6/1994   Morgan et al. .

FOREIGN PATENT DOCUMENTS

| 0 541 952 | 5/1993 | (EP) . |
|---|---|---|
| 0 668 352 | 8/1995 | (EP) . |
| WO 93/18066 | 9/1993 | (WO) . |
| WO 96/11951 | 4/1996 | (WO) . |
| WO 96/15146 | 5/1996 | (WO) . |

OTHER PUBLICATIONS

Supersaxo et al., Pharmaceutical Research, vol. 7, No. 2, pp. 167–169 (1990).

Kang et al., Diabetes Care, vol. 14, No. 11, pp. 942–948 (1991).

Brange et al., Nature, vol. 333, pp. 679–682 (1988).

Holland et al., Journal of Molecular Biology, vol. 239, pp. 385–400 (1994).

Ibañez et al., Cell, vol. 69, pp. 329–341 (1992).

Ibañez et al., The EMBO Journal, vol. 12, No. 6, pp. 2281–2293 (1993).

Lomko, Drug News and Perspectives, vol. 6, No. 9, pp. 669–671 (1993).

Maisonpierre et al., Genomics, vol. 10, No. 3, pp. 558–568 (1991).

*Primary Examiner*—Albert Navarro
*Assistant Examiner*—Li Lee
(74) *Attorney, Agent, or Firm*—Richard J. Mazza; Ron K. Levy; Steven M. Odre

(57) ABSTRACT

The in vivo circulating life and/or absorption of the cationic therapeutic protein BDNF can be increased by generating analogs that have a lower isoelectric point and, preferably, also a lower protein charge relative to the protein of native sequence.

13 Claims, 11 Drawing Sheets

FIG. 1

Figure 4:
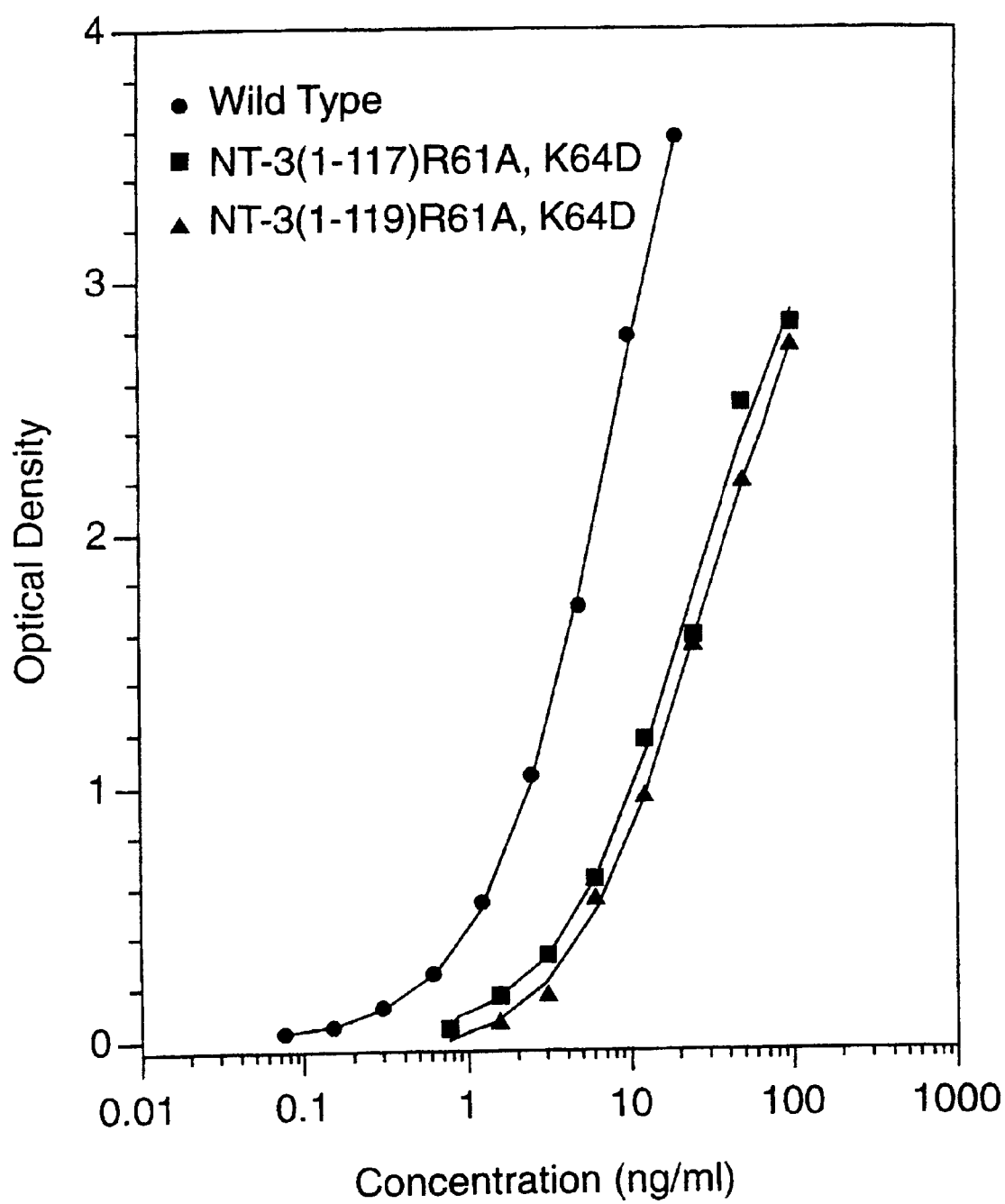

Met Tyr Ala Glu His Lys Ser His Arg Gly Glu Tyr Ser Val Cys Asp
-1            5                10                 15

Ser Glu Ser Leu Trp Val Thr Asp Lys Ser Ser Ala Ile Asp Ile Arg
                20              25                  30

Gly His Gln Val Thr Val Leu Gly Glu Ile Lys Thr Gly Asn Ser Pro
            35              40                  45

Val Lys Gln Tyr Phe Tyr Glu Thr Arg Cys Lys Glu Ala Arg Pro Val
        50              55                  60

Lys Asn Gly Cys Arg Gly Ile Asp Asp Lys His Trp Asn Ser Gln Cys
    65              70              75

Lys Thr Ser Gln Thr Tyr Val Arg Ala Leu Thr Ser Glu Asn Asn Lys
80              85              90                  95

Leu Val Gly Trp Arg Trp Ile Arg Ile Asp Thr Ser Cys Val Cys Ala
                100             105                 110

Leu Ser Arg Lys Ile Gly Arg Thr
            115

FIG.2A

| | | | | | | |
|---|---|---|---|---|---|---|
| ATGTACGCTG | AACACAAATC | TCACCGTGGT | GAATACTCTG | TTTGCGACTC | TGAATCTCTG | 60 |
| TGGGTTACCG | ACAAATCTTC | TGCTATCGAC | ATCCGTGGTC | ACCAGGTTAC | CGTTCTGGGT | 120 |
| GAAATCAAAA | CCGGTAACTC | TCCGGTTAAA | CAGTACTTCT | ACGAAACCCG | TTGCAAAGAA | 180 |
| GCTGCACCGG | TTGACAACGG | TTGCCGTGGT | ATCGACGACA | AACACTGGAA | CTCTCAGTGC | 240 |
| AAAACCTCTC | AGACCTACGT | TCGTGCTCTG | ACCTCTGAAA | ACAACAAGCT | TGTTGGTTGG | 300 |
| CGTTGGATTC | GTATCGACAC | CTCTTGCGTT | TGCGCTCTGT | CTCGTAAAAT | CGGTCGTACC | 360 |

FIG. 2B

Met Tyr Ala Glu His Lys Ser His Arg Gly Glu Tyr Ser Val Cys Asp
-1              5                   10                      15

Ser Glu Ser Leu Trp Val Thr Asp Lys Ser Ser Ala Ile Asp Ile Arg
                20                  25                      30

Gly His Gln Val Thr Val Leu Gly Glu Ile Lys Thr Gly Asn Ser Pro
                35                  40                      45

Val Lys Gln Tyr Phe Tyr Glu Thr Arg Cys Lys Glu Ala Ala Pro Val
                50                  55                      60

Asp Asn Gly Cys Arg Gly Ile Asp Asp Lys His Trp Asn Ser Gln Cys
65                  70                  75

Lys Thr Ser Gln Thr Tyr Val Arg Ala Leu Thr Ser Glu Asn Asn Lys
80                  85                  90                      95

Leu Val Gly Trp Arg Trp Ile Arg Ile Asp Thr Ser Cys Val Cys Ala
                100                 105                     110

Leu Ser Arg Lys Ile Gly Arg Thr
                115

FIG. 3A

```
ATGTACGCTG AACACAAATC TCACCGTGGT GAATACTCTG TTTGCGACTC TGAATCTCTG        60

TGGGTTACCG ACAAATCTTC TGCTATCGAC ATCCGTGGTC ACCAGGTTAC CGTTCTGGGT       120

GAAATCAAAA CCGGTAACTC TCCGGTTAAA CAGTACTTCT ACGAAACCCG TTGCAAAGAA       180

GCTGCACCGG TTGACAACGG TTGCCGTGGT ATCGACGACA AACACTGGAA CTCTCAGTGC       240

AAAACCTCTC AGACCTACGT TCGTGCTCTG ACCTCTGAAA CAACAAGCT TGTTGGTTGG       300

CGTTGGATTC GTATCGACAC CTCTTGCGTT TGCGCTCTGT CTCGTAAAAT CGGT           354
```

FIG. 3B

Met Tyr Ala Glu His Lys Ser His Arg Gly Glu Tyr Ser Val Cys Asp
-1            5                   10                  15

Ser Glu Ser Leu Trp Val Thr Asp Lys Ser Ser Ala Ile Asp Ile Arg
               20                  25                  30

Gly His Gln Val Thr Val Leu Gly Glu Ile Lys Thr Gly Asn Ser Pro
                35                  40                  45

Val Lys Gln Tyr Phe Tyr Glu Thr Arg Cys Lys Glu Ala Ala Pro Val
            50                  55                  60

Asp Asn Gly Cys Arg Gly Ile Asp Asp Lys His Trp Asn Ser Gln Cys
        65                  70                  75

Lys Thr Ser Gln Thr Tyr Val Arg Ala Leu Thr Ser Glu Asn Asn Lys
80                  85                  90                  95

Leu Val Gly Trp Arg Trp Ile Arg Ile Asp Thr Ser Cys Val Cys Ala
                100                 105                 110

Leu Ser Arg Lys Ile Gly
            115

SEQUENCE LISTING

<160> NUMBER OF SEQ ID NOS: 12

<210> SEQ ID NO 1
<211> LENGTH: 120
<212> TYPE: PRT
<213> ORGANISM: Human

<400> SEQUENCE: 1

| Met | Tyr | Ala | Glu | His | Lys | Ser | His | Arg | Gly | Glu | Tyr | Ser | Val | Cys | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Glu | Ser | Leu | Trp | Val | Thr | Asp | Lys | Ser | Ser | Ala | Ile | Asp | Ile | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | His | Gln | Val | Thr | Val | Leu | Gly | Glu | Ile | Lys | Thr | Gly | Asn | Ser | Pro |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Val | Lys | Gln | Tyr | Phe | Tyr | Glu | Thr | Arg | Cys | Lys | Glu | Ala | Arg | Pro | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Asn | Gly | Cys | Arg | Gly | Ile | Asp | Asp | Lys | His | Trp | Asn | Ser | Gln | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Thr | Ser | Gln | Thr | Tyr | Val | Arg | Ala | Leu | Thr | Ser | Glu | Asn | Asn | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Val | Gly | Trp | Arg | Trp | Ile | Arg | Ile | Asp | Thr | Ser | Cys | Val | Cys | Ala |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Leu | Ser | Arg | Lys | Ile | Gly | Arg | Thr |
|-----|-----|-----|-----|-----|-----|-----|-----|
|     |     |     | 115 |     |     |     | 120 |

<210> SEQ ID NO 2
<211> LENGTH: 360
<212> TYPE: DNA
<213> ORGANISM: Human

<400> SEQUENCE: 2

```
atgtacgctg aacacaaatc tcaccgtggt gaatactctg tttgcgactc tgaatctctg      60
tgggttaccg acaaatcttc tgctatcgac atccgtggtc accaggttac cgttctgggt    120
gaaatcaaaa ccggtaactc tccggttaaa cagtacttct acgaaacccg ttgcaaagaa    180
gctgcaccgg ttgacaacgg ttgccgtggt atcgacgaca acactggaa ctctcagtgc    240
aaaacctctc agacctacgt tcgtgctctg acctctgaaa acaacaagct tgttggttgg    300
cgttggattc gtatcgacac ctcttgcgtt tgcgctctgt ctcgtaaaat cggtcgtacc    360
```

<210> SEQ ID NO 3
<211> LENGTH: 120
<212> TYPE: PRT
<213> ORGANISM: Human

<400> SEQUENCE: 3

| Met | Tyr | Ala | Glu | His | Lys | Ser | His | Arg | Gly | Glu | Tyr | Ser | Val | Cys | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Glu | Ser | Leu | Trp | Val | Thr | Asp | Lys | Ser | Ser | Ala | Ile | Asp | Ile | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | His | Gln | Val | Thr | Val | Leu | Gly | Glu | Ile | Lys | Thr | Gly | Asn | Ser | Pro |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Val | Lys | Gln | Tyr | Phe | Tyr | Glu | Thr | Arg | Cys | Lys | Glu | Ala | Ala | Pro | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Asn | Gly | Cys | Arg | Gly | Ile | Asp | Asp | Lys | His | Trp | Asn | Ser | Gln | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

```
Lys Thr Ser Gln Thr Tyr Val Arg Ala Leu Thr Ser Glu Asn Asn Lys
                85                  90                  95
Leu Val Gly Trp Arg Trp Ile Arg Ile Asp Thr Ser Cys Val Cys Ala
            100                 105                 110
Leu Ser Arg Lys Ile Gly Arg Thr
        115                 120
```

<210> SEQ ID NO 4
<211> LENGTH: 354
<212> TYPE: DNA
<213> ORGANISM: Human

<400> SEQUENCE: 4

```
atgtacgctg aacacaaatc tcaccgtggt gaatactctg tttgcgactc tgaatctctg      60
tgggttaccg acaaatcttc tgctatcgac atccgtggtc accaggttac cgttctgggt    120
gaaatcaaaa ccggtaactc tccggttaaa cagtacttct acgaaacccg ttgcaaagaa    180
gctgcaccgg ttgacaacgg ttgccgtggt atcgacgaca acactggaa ctctcagtgc     240
aaaacctctc agacctacgt tcgtgctctg acctctgaaa acaacaagct tgttggttgg    300
cgttggattc gtatcgacac ctcttgcgtt tgcgctctgt ctcgtaaaat cggt           354
```

<210> SEQ ID NO 5
<211> LENGTH: 118
<212> TYPE: PRT
<213> ORGANISM: Human

<400> SEQUENCE: 5

```
Met Tyr Ala Glu His Lys Ser His Arg Gly Glu Tyr Ser Val Cys Asp
 1               5                  10                  15
Ser Glu Ser Leu Trp Val Thr Asp Lys Ser Ser Ala Ile Asp Ile Arg
            20                  25                  30
Gly His Gln Val Thr Val Leu Gly Glu Ile Lys Thr Gly Asn Ser Pro
        35                  40                  45
Val Lys Gln Tyr Phe Tyr Glu Thr Arg Cys Lys Glu Ala Ala Pro Val
     50                 55                  60
Asp Asn Gly Cys Arg Gly Ile Asp Asp Lys His Trp Asn Ser Gln Cys
 65                 70                  75                  80
Lys Thr Ser Gln Thr Tyr Val Arg Ala Leu Thr Ser Glu Asn Asn Lys
                85                  90                  95
Leu Val Gly Trp Arg Trp Ile Arg Ile Asp Thr Ser Cys Val Cys Ala
            100                 105                 110
Leu Ser Arg Lys Ile Gly
        115
```

<210> SEQ ID NO 6
<211> LENGTH: 119
<212> TYPE: PRT
<213> ORGANISM: Human

<400> SEQUENCE: 6

```
Tyr Ala Glu His Lys Ser His Arg Gly Glu Tyr Ser Val Cys Asp Ser
 1               5                  10                  15
Glu Ser Leu Trp Val Thr Asp Lys Ser Ser Ala Ile Asp Ile Arg Gly
            20                  25                  30
His Gln Val Thr Val Leu Gly Glu Ile Lys Thr Gly Asn Ser Pro Val
        35                  40                  45
Lys Gln Tyr Phe Tyr Glu Thr Arg Cys Lys Glu Ala Ala Pro Val Asp
```

-continued

```
            50                  55                  60
Asn Gly Cys Arg Gly Ile Asp Asp Lys His Trp Asn Ser Gln Cys Lys
 65                  70                  75                  80

Thr Ser Gln Thr Tyr Val Arg Ala Leu Thr Ser Glu Asn Asn Lys Leu
                 85                  90                  95

Val Gly Trp Arg Trp Ile Arg Ile Asp Thr Ser Cys Val Cys Ala Leu
                100                 105                 110

Ser Arg Lys Ile Gly Arg Thr
            115

<210> SEQ ID NO 7
<211> LENGTH: 117
<212> TYPE: PRT
<213> ORGANISM: Human

<400> SEQUENCE: 7

Tyr Ala Glu His Lys Ser His Arg Gly Glu Tyr Ser Val Cys Asp Ser
  1               5                  10                  15

Glu Ser Leu Trp Val Thr Asp Lys Ser Ser Ala Ile Asp Ile Arg Gly
                 20                  25                  30

His Gln Val Thr Val Leu Gly Glu Ile Lys Thr Gly Asn Ser Pro Val
                 35                  40                  45

Lys Gln Tyr Phe Tyr Glu Thr Arg Cys Lys Glu Ala Ala Pro Val Asp
         50                  55                  60

Asn Gly Cys Arg Gly Ile Asp Asp Lys His Trp Asn Ser Gln Cys Lys
 65                  70                  75                  80

Thr Ser Gln Thr Tyr Val Arg Ala Leu Thr Ser Glu Asn Asn Lys Leu
                 85                  90                  95

Val Gly Trp Arg Trp Ile Arg Ile Asp Thr Ser Cys Val Cys Ala Leu
                100                 105                 110

Ser Arg Lys Ile Gly
            115

<210> SEQ ID NO 8
<211> LENGTH: 120
<212> TYPE: PRT
<213> ORGANISM: Human

<400> SEQUENCE: 8

Met His Ser Asp Pro Ala Arg Arg Gly Glu Leu Ser Val Cys Asp Ser
  1               5                  10                  15

Ile Ser Glu Trp Val Thr Ala Ala Asp Lys Lys Thr Ala Val Asp Met
                 20                  25                  30

Ser Gly Gly Thr Val Thr Val Leu Glu Lys Val Pro Val Ser Lys Gly
                 35                  40                  45

Gln Leu Lys Gln Tyr Phe Tyr Glu Thr Lys Cys Asn Pro Met Gly Tyr
         50                  55                  60

Thr Lys Glu Gly Cys Arg Gly Ile Asp Lys Arg His Trp Asn Ser Gln
 65                  70                  75                  80

Cys Arg Thr Thr Gln Ser Tyr Val Arg Ala Leu Thr Met Asp Ser Lys
                 85                  90                  95

Lys Arg Ile Gly Trp Arg Phe Ile Arg Ile Asp Thr Ser Cys Val Cys
                100                 105                 110

Thr Leu Thr Ile Lys Arg Gly Arg
            115                 120
```

<210> SEQ ID NO 9
<211> LENGTH: 120
<212> TYPE: PRT
<213> ORGANISM: Human

<400> SEQUENCE: 9

```
Met His Ser Asp Pro Ala Arg Arg Gly Glu Leu Ser Val Cys Asp Ser
  1               5                  10                  15

Ile Ser Glu Trp Val Thr Ala Ala Asp Lys Lys Thr Ala Val Asp Met
             20                  25                  30

Ser Gly Gly Thr Val Thr Val Leu Glu Lys Val Pro Val Ser Lys Gly
         35                  40                  45

Gln Leu Lys Gln Tyr Phe Tyr Glu Thr Lys Cys Asn Pro Met Gly Tyr
     50                  55                  60

Thr Asp Glu Gly Cys Arg Gly Ile Asp Asp Arg His Trp Asn Ser Gln
 65                  70                  75                  80

Cys Arg Thr Thr Gln Ser Tyr Val Arg Ala Leu Thr Met Asp Ser Ala
                 85                  90                  95

Lys Ala Ile Gly Trp Arg Phe Ile Arg Ile Asp Thr Ser Cys Val Cys
            100                 105                 110

Thr Leu Thr Ile Lys Arg Gly Arg
        115                 120
```

<210> SEQ ID NO 10
<211> LENGTH: 120
<212> TYPE: PRT
<213> ORGANISM: Human

<400> SEQUENCE: 10

```
Met His Ser Asp Pro Ala Arg Arg Gly Glu Leu Ser Val Cys Asp Ser
  1               5                  10                  15

Ile Ser Glu Trp Val Thr Ala Ala Asp Lys Lys Thr Ala Val Asp Met
             20                  25                  30

Ser Gly Gly Thr Val Thr Val Leu Glu Lys Val Pro Val Ser Lys Gly
         35                  40                  45

Gln Leu Lys Gln Tyr Phe Tyr Glu Thr Lys Cys Asn Glu Met Gly Tyr
     50                  55                  60

Thr Asp Glu Gly Cys Arg Gly Ile Asp Asp Arg His Trp Asn Ser Gln
 65                  70                  75                  80

Cys Arg Thr Thr Gln Ser Tyr Val Arg Ala Leu Thr Met Asp Ser Ala
                 85                  90                  95

Lys Arg Ile Gly Trp Arg Phe Ile Arg Ile Asp Thr Ser Cys Val Cys
            100                 105                 110

Thr Leu Thr Ile Lys Arg Gly Arg
        115                 120
```

<210> SEQ ID NO 11
<211> LENGTH: 663
<212> TYPE: DNA
<213> ORGANISM: Artificial Sequence
<220> FEATURE:
<223> OTHER INFORMATION: Description of Artificial Sequence: Hybrid of
      bacterial (E. coli) and human (Homo sapiens)
      sequence.

<400> SEQUENCE: 11

```
cgtaacgtat gcatggtctc cccatgcgag agtagggaac tgccaggcat caataaaacg      60
aaaggctcag tcgaaagact gggcctttcg ttttatctgt tgtttgtcgg tgacgctctc     120
```

```
ctgagtagga caaatccgcc gggagcggat ttgaacgttg cgaagcaacg gccggagggt     180
ggcgggcagg acgcccgcca taaactgcca ggcatcaaat taagcagaag ccatcctgac     240
ggatggcctt tttgcgtttc tacaaactct tttgtttatt tttctaaata cattcaaata     300
tggacgtctc ataatttta aaaaattcat ttgacaaatg ctaaaattct tgattaatat     360
tctcaattgt gagcgctcac aatttatcga tttgattcta gatttgagtt ttaacttta     420 gaaggaggaa taacatatgg ttaacgcgtt ggaattcgag ctcactagtg tcgacctgca     480
gggtaccatg gaagcttact cgaggatccg cggaaagaag aagaagaaga agaaagcccg     540
aaaggaagct gagttggctg ctgccaccgc tgagcaataa ctagcataac cccttggggc     600
ctctaaacgg gtcttgaggg gttttttgct gaaaggagga accgctcttc acgctcttca     660
cgc                                                                   663
```

```
<210> SEQ ID NO 12
<211> LENGTH: 665
<212> TYPE: DNA
<213> ORGANISM: Artificial Sequence
<220> FEATURE:
<223> OTHER INFORMATION: Description of Artificial Sequence: Hybrid of
      bacterial (E. coli) and human (Homo sapiens)
      sequence.

<400> SEQUENCE: 12
```

```
gtgaagagcg tgaagagcgg ttcctccttt cagcaaaaaa cccctcaaga cccgtttaga      60
ggccccaagg ggttatgcta gttattgctc agcggtggca gcagccaact cagcttcctt     120
tcgggctttc ttcttcttct tcttctttcc gcggatcctc gagtaagctt ccatggtacc     180
ctgcaggtcg acactagtga gctcgaattc caacgcgtta accatatgtt attcctcctt     240
ctaaaagtta aaactcaaat ctagaatcaa atcgataaat tgtgagcgct cacaattgag     300
aatattaatc aagaatttta gcatttgtca aatgaatttt ttaaaaatta tgagacgtcc     360
atatttgaat gtattagaaa aataaacaaa agagtttgta gaaacgcaaa aaggccatcc     420
gtcaggatgg ccttctgctt aatttgatgc ctggcagttt atggcgggcg tcctgcccgc     480
caccctccgg ccgttgcttc gcaacgttca aatccgctcc cggcggattt gtcctactca     540
ggagagcgtc accgacaaac aacagataaa acgaaaggcc cagtctttcg actgagcctt     600
tcgttttatt gatgcctggc agttccctac tctcgcatgg ggagaccatg catacgttac     660
gcacg                                                                 665
```

ANALOGS OF CATIONIC PROTEINS

This application is a 371 CFR National Stage Filing of PCT/US97/12609, filed Jul. 17, 1997, which is a continuation-in-part of U.S. application Ser. No. 08/684, 353, filed Jul. 19, 1996, now abandoned.

FIELD OF THE INVENTION

This invention relates generally to polypeptide analogs of therapeutically active cationic proteins, including but not limited to analogs of the neurotrophic factors known as neurotrophin-3 (NT-3) and brain-derived neurotrophic factor (BDNF). More specifically, the invention relates to positively charged polypeptides in which modifications have been made in the native sequence, such that the analogs possess lower isoelectric points and, concomitantly, longer circulation times and/or improved absorption in vivo following parenteral administration. The invention also relates to materials and methods for the recombinant production of such polypeptide analogs, to antibodies thereof, and to pharmaceutical compositions containing the analogs which can be used for the treatment of various diseases and disorders.

BACKGROUND OF THE INVENTION

Following the administration of a therapeutic protein by parenteral means, such as by subcutaneous, intravenous or intramuscular injection, the pharmacokinetic properties such as bioavailability, circulation time and clearance rate can vary widely from protein to protein. Even though there are active efforts in many laboratories to develop alternative routes of administration for protein products, little is known about the factors that govern the pharmacokinetic behavior of protein therapeutics following such parenteral administration. It has been shown that an increase in the molecular weight of a protein can result in a preferential uptake by the lymphatic system rather than the blood capillaries; Supersaxo et al., Pharmaceutical Res., Volume 7, page 167 et seq. (1990). The molecular size of the therapeutic protein also plays a key role in insulin uptake, where dissociation of a zinc-induced hexamer to monomeric form has been shown to be the rate-limiting step in insulin absorbance; Kang et al., Diabetes Care, Volume 14, pages 942–948 (1991). The clinical testing in diabetic patients of monomeric insulin analogs, in which the hexamer association site has been eliminated, has demonstrated a more rapid uptake, leading to significant improvements in glucose control in diabetic patients; see Brange et al., Nature, Volume 333, page 679 et seq. (1988).

SUMMARY OF THE INVENTION

To assess the impact of the isoelectric point (pI) on the pharmacokinetic behavior of proteins, certain analogs of NT-3 and BDNF, in particular, have been produced which have a relatively lower pI, yet retain the structure and biological activity of the protein in its "native" state (i.e., the protein of naturally occurring amino acid sequence, as well as the $met^{-1}$ version thereof, both of which are referred to herein as "wild type"). From these studies, it has now been discovered that protein analogs engineered to possess a lower pI and/or lower charge under physiological conditions than the wild type molecule, can also display longer in vivo circulation times (i.e., "half life") and improved absorption following administration by injection. Although the invention is illustrated in this description with particular reference to human NT-3 and BDNF, it has broader applicability to any cationic proteins, and particularly basic proteins which in their native sequence have a pI greater than about 7.0.

It should be noted that the terms "protein" and "polypeptide" are used interchangeably throughout this description to mean one and the same thing.

Briefly stated, the present invention is concerned with substitution, insertion and deletion analogs of cationic therapeutic proteins, and/or chemically modified versions of such therapeutic proteins, that are characterized by a lower pI while also exhibiting longer circulation times and/or higher absorption relative to the unmodified proteins (i.e., of native sequence). The analog proteins of this invention are typically human therapeutic proteins which are usually, but not necessarily, basic proteins. Preferably, these proteins also have a lower charge under physiological conditions compared to the unmodified basic protein.

The present invention also concerns materials and methods for the recombinant production of such analogs (as a preferred practical method), as well as to antibodies raised against the protein analogs, and to pharmaceutical compositions containing the analogs as biologically active agents for use in the treatment of diseases and physical disorders.

BRIEF DESCRIPTION OF THE DRAWINGS

FIG. 1 shows the amino acid sequence for wild type human NT-3 (i.e., of "native" sequence) which has been produced recombinantly in *E. coli* bacterial cells and expressed with a methionine residue present at the N-terminus, i.e., r-metHuNT-3 (SEQ ID NO: 1). In the Figure, the amino acid numbering begins with the first residue after the initial methicnine ($Met^{-1}$), since the naturally occurring protein is normally expressed in mammalian cells without the methionine residue. (Note that Sequence Listing herein counts Met residue as +1).

FIG. 2 shows the nucleic acid sequence (SEQ ID NO: 2, and FIG. 2A) and amino acid sequence (SEQ ID NO: 3, and FIG. 2B) of a polypeptide analog of r-metHuNT-3 of the present invention, namely, $NT\text{-}3_{(1\text{-}119)}$R61A,K64D (with amino acid numbering in the Figure beginning with first residue after initial methionine).

FIG. 3 shows the nucleic acid sequence (SEQ ID NO: 4, and FIG. 3A) and amino acid sequence (SEQ ID NO: 5, and FIG. 3B) of another polypeptide analog of r-metHuNT-3 according to the present invention, namely, $NT\text{-}3_{(1\text{-}117)}$ R61A,K64D (amino acid numbering in Figure again beginning with first residue after initial methionine).

FIG. 4 shows the ELISA assay calibration (standard) curves for wild type NT-3 (i.e., having SEQ ID NO: 1) and for the NT-3 analogs of SEQ ID NOS: 3 and 5. The optical density is plotted against sample concentration in nanograms per milliliter (ng/ml). The cross-reactivity to NT-3 analogs in the ELISA assay is approximately ten percent. Serum samples from pharmacokinetic studies were analyzed by ELISA, and concentrations of wild type NT-3 and NT-3 analogs were determined by calibration against the appropriate standard curve.

FIG. 5 depicts a size exclusion high performance liquid chromatogram (SEC-HPLC) in which wild type NT-3 is compared to the NT-3 analogs of FIGS. 2 and 3. Units of absorbance ("AU") are plotted on the vertical axis, and the time of elution to the peak (in minutes) is shown on the horizontal axis. As shown, the analogs co-elute with the wild type molecule, demonstrating that the noncovalent dimer structure of wild type NT-3 has not been disrupted in either of the analogs. No aggregated protein was detected in any of these preparations. Figure legends: (_____) wild type NT-3; (----) $NT\text{-}3_{(1\text{-}117)}$R61A,K64D; and (_·_) $NT\text{-}3_{(1\text{-}119)}$R61A, K64D.

Figure 6:
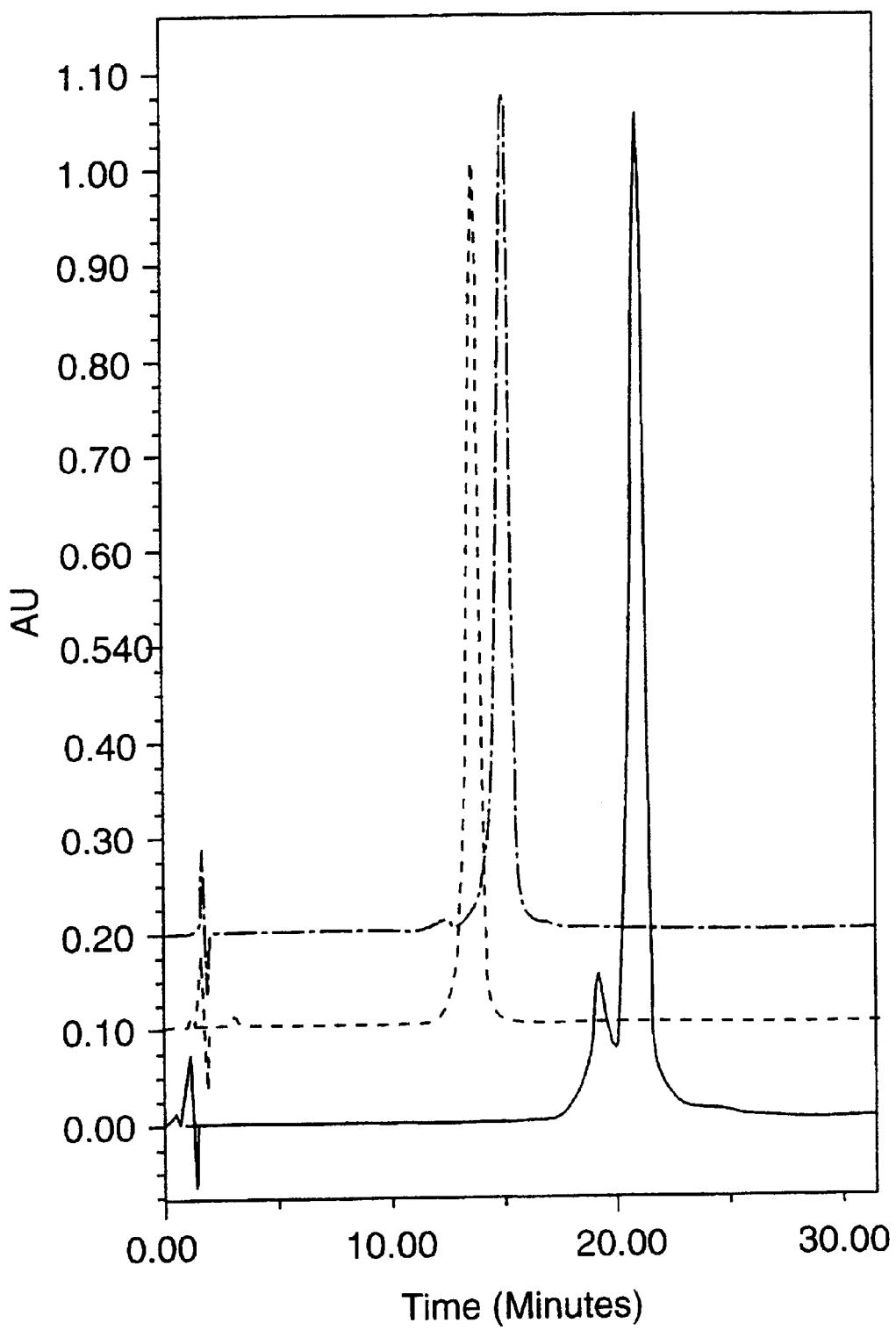

FIG. 6 depicts a cation exchange high performance liquid chromatogram (CEX-HPLC) in which wild type NT-3 is compared to the NT-3 analogs of FIGS. 2 and 3. "AU" (vertical axis) indicates absorbance units. Time of elution to peak is shown on the horizontal axis. In this figure the analogs elute sooner than wild type NT-3, which is consistent with the lower isoelectric points of the analogs. Figure legends: (_____) wild type NT-3; (----) NT-3$_{(1-117)}$R61A, K64D; and (_·_) NT-3$_{(1-119)}$R61A,K64D.

Figure 7:
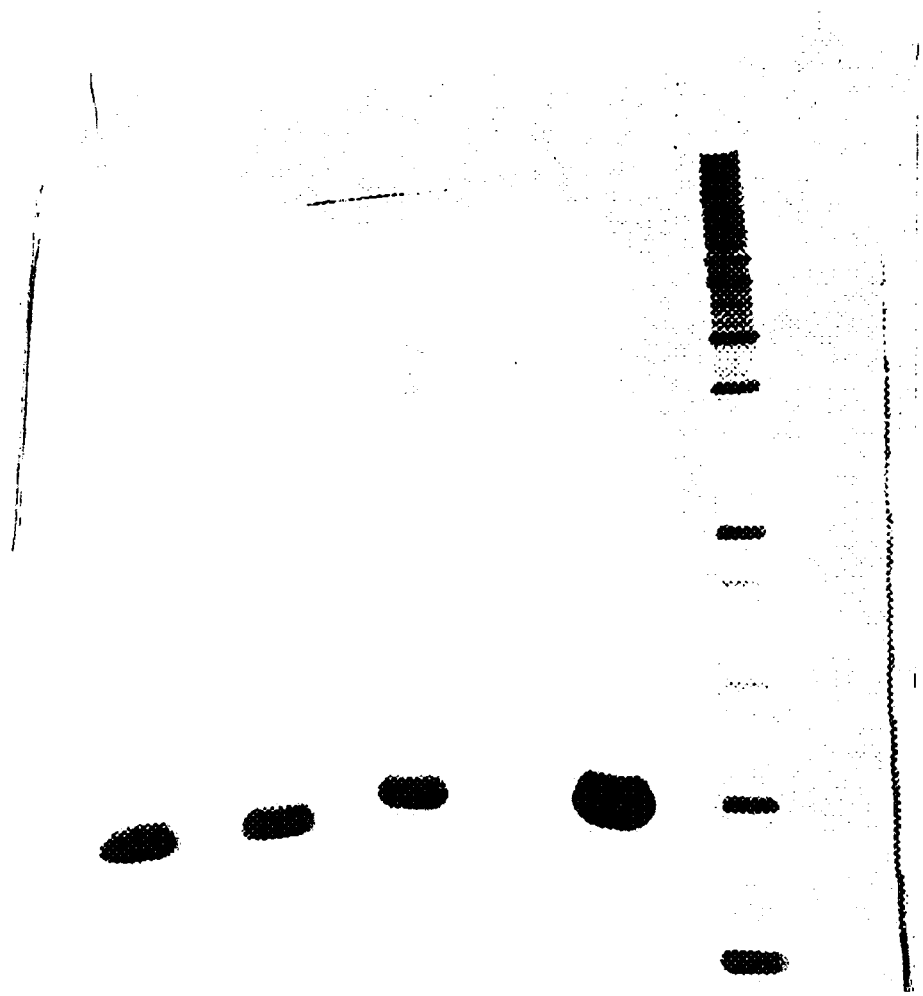

FIG. 7 depicts a silver stained SDS polyacrylamide gel electrophoresis (SDS-PAGE) chromatogram in which wild type NT-3 (see FIG. 1) is compared to the NT-3 analogs of FIGS. 2 and 3. All three samples run as a single band with approximately the same molecular weight of the monomeric form. None of the samples are seen to contain significant amounts of higher molecular weight oligomers or lower molecular weight fragments. Lane 1: NT-3$_{(1-117)}$R61A, K64D, 2.5 µg; Lane 2: NT-3$_{(1-119)}$R61A,K64D, 2.5 µg; Lane 3; wild type NT-3, 2.5 µg; Lane 4: wild type NT-3, 12.5 µg; Lane 5: molecular weight markers.

Figure 8:
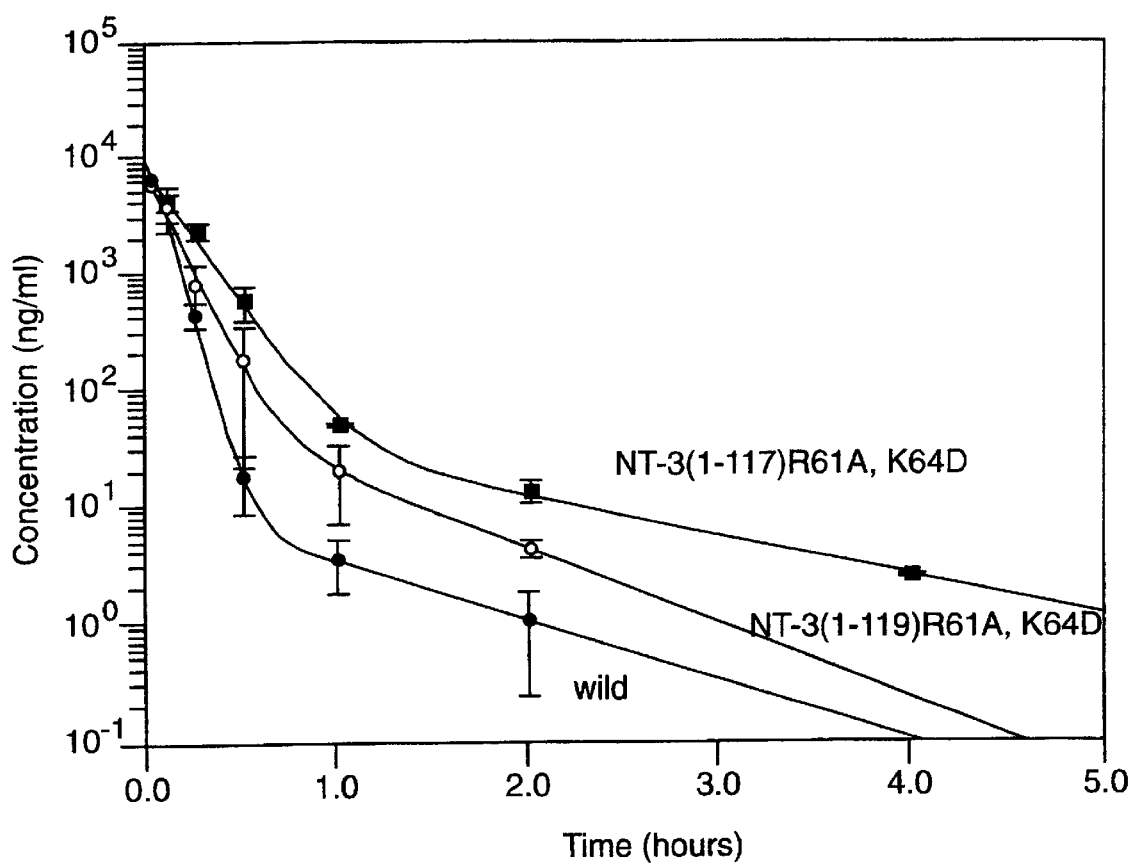

FIG. 8 shows the serum concentration (in nanograms per milliliter) versus time(in hours) profiles for the proteins of SEQ ID NOS: 1, 3 and 5 after intravenous (IV) administration to test rats. The dose level was 1 milligram per kilogram (mg/kg) of body weight. The concentration profiles are biphasic. The initial distribution phase was followed by a slower elimination phase. Each point on the graph represents an average of three animals.

Figure 9:
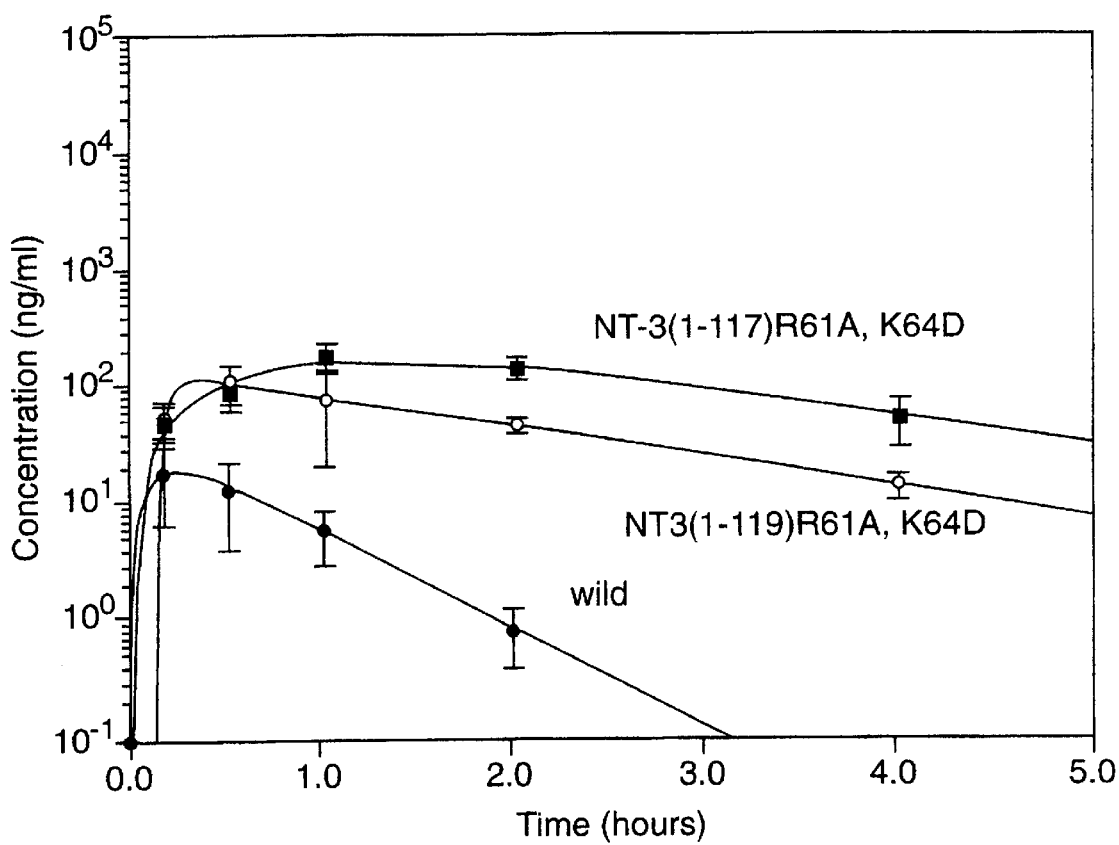

FIG. 9 shows the serum concentration (in nanograms per milliliter) versus time (in hours) curves in rats for the proteins of SEQ ID NOS: 1, 3 and 5 following subcutaneous (SC) administration of 1 mg/kg, with each point on the graph again representing an average of three animals. The absorption phase is characterized by an increase in serum concentration to a peak. Wild type NT-3 (SEQ ID NO: 1) showed the most rapid decline after attaining maximal concentration.

DETAILED DESCRIPTION OF THE INVENTION

The principles of this invention have broad applicability to any cationic proteins for which a reduction in the pI and, optionally, protein charge will result in an enhancement of therapeutically relevant biological properties such as circulation time and/or absorption following parenteral administration. By way of illustration, such proteins include but are not limited to basic proteins such as NT-3, BDNF, macrophage growth and differentiation factor and various known isoforms thereof having essentially the same ability to increase blood platelet production in vivo and ex vivo (referred to herein collectively as "MGDF"), and keratinocyte growth factor (KGF). Detailed descriptions of these factors, their biological properties, and methods for their preparation and testing are given in the patent literature: NT-3 in published PCT application WO 91/03569; BDNF in U.S. Pat. No. 5,180,820, U.S. Pat. No. 5,229,500, U.S. Pat. No. 5,438,121 and U.S. Pat. No. 5,453,361, and in published PCT application w70 91/03568; MGDF in published PCT applications WO 95/26745, WO 95/21919, and WO 95/21920; and KGF in published PCT application WO 90/08771.

In essence, the objective of this invention is to make one or more modifications to the primary structure of the wild type protein that preserve the protein structure and biological activity of the protein, but which also results in a lower isoelectric point and, preferably, a lower charge at physiological pH. The particular way in which these modifications are made is not critical, and any procedure can be used which effects the aforementioned changes to achieve the described enhancements in properties. Merely by way of illustration, appropriate modifications can be accomplished by use of site directed mutagenesis involving the addition of acidic residues to the sequence by insertion and/or replacement mutations, and/or removal of basic residues by deletion and/or replacement mutations. Alternatively, chemical groups or moieties can be added to selected sites (i.e., on amino acid residues) in the protein chain of the wild type molecule to accomplish the same end purpose (i.e., reduction of pI and charge with preservation of structure and biological activity). A specific example is the succinviation of selected residues in the protein chain.

Nucleic acids which encode protein analogs in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Ausubel et al., editors, Current Protocols in Molecular Biology, Green Publishers Inc. and Wiley and Sons, NY (1994). Chemical synthesis using methods described by Engels et al. in Angew. Chem. Intl. Ed., Volume 28, pages 716–734 (1989), may also be used to prepare such nucleic acids.

The DNA molecules may be used to express the analog polypeptides of the invention by recombinant methods familiar to those skilled in the art, including but not limited to methods described in the above mentioned patents or patent applications for NT-3, BDNF, KGF and MGDF. By way of illustration, a nucleic acid sequence encoding an analog polypeptide of this invention is inserted into an appropriate biologically functional vector (e.g., circular piasmid or viral DNA) for expression in a suitable host cell. The vector includes regulatory sequences for expression of the inserted nucleic acid sequence and is selected to be functional in the particular host cell employed (i.e., the vector is compatible with the host cell machinery, such that amplification and/or expression of the gene can occur). The polypeptide may be amplified/expressed in prokaryotic, yeast, insect (baculovirus systems) and/or eukaryotic host cells. Selection of the host cell will depend at least in part on whether the polypeptide expression product is to be glycosylated. If glycosylation is desired, then yeast, insect or mammalian host cells are preferred for use.

Typically, the vectors will contain a 5' flanking sequence (also referred to as a "promoter") and other regulatory elements, as well as enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element.

The 5' flanking sequence may be the innate 5' flanking sequence from the wild type gene, or it may be homologous (i.e., from the same species and/or strain as the host cell), heterologous (i.e., from a species other than the host cell species or strain), hybrid (i.e., a combination of 5' flanking sequences from more than one source), or synthetic. The source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The origin of replication element is typically a part of prokaryotic expression vectors purchased commercially, and aids in the amplification of the vector in a host cell. Amplification of the vector to a certain copy number can, in some cases, be important for optimal expression of the polypeptide. If the vector of choice does not contain an origin of replication site, one may be chemically synthesized based on a known sequence and then ligated into the vector.

The transcription termination element is typically located 3' to the end of the polypeptide coding sequence and serves to terminate transcription of the polypeptide. Usually, the transcription termination element in prokaryotic cells is a G-C rich fragment followed by a poly-T sequence. While the element is easily cloned from a library or even purchased commercially as part of a vector, it can also be readily synthesized using methods for nucleic acid synthesis such as those referred to above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (for prokaryotes) or the Kozak sequence (for eukaryotes), is necessary for the initiation of translation for mRNA. The element is typically located 3' to the promoter and 5' to the coding sequence of the polypeptide to be synthesized. The Shine-Dalgarno sequence is varied but is typically a polypurine (i.e., having a high A–G content). Many Shine-Dalgarno sequences have been identified, each of which can be readily synthesized using methods set forth above and used in a prokaryotic vector.

In those cases where it is desirable for the polypeptide to be secreted from the host cell, a signal sequence may be used to direct the polypepcide out of the host cell where it is synthesized. Typically, the signal sequence is positioned in the coding region of nucleic acid sequence, or directly at the 5' end of the coding region. Many signal sequences have been identified, and any of them that are functional in the selected host cell may be used here. Consequently, the signal sequence may be homologous or heterologous to the polypeptide. Additionally, the signal sequence may be chemically synthesized using methods such as those referred to set above.

Host cells may be prokaryotic host cells (such as *E. coli*) or eukaryotic host cells (such as yeast, insect or vertebrate cells). The host cell, when cultured under suitable nutrient conditions, can synthesize the polypeptide, which can subsequently be collected by isolation from the culture medium (if the host cell secretes it into the medium) or directly from the host cell producing it (if not secreted). After collection, the polypeptide can be purified using methods such as molecular sieve chromatography, affinity chromatography, and the like. In general, if the polypeptide is expressed in *E. coli* it will contain a methionine residue at the N-terminus in its recovered form (i.e. met$^{-1}$), unless expressed in a strain of *E. coli* in which the methionine is enzymatically cleaved off by the host.

Suitable cells or cell lines may also be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or they may contain a dominantly acting selection gene. Still other suitable mammalian cell lines include but are not limited to, HeLa, mouse L-929 cells, 3T3 lines derived from Swiss, Balb-c or NIH mice, BHK or HaK hamster cell lines.

Insertion (also referred to as "transformation" or "transfection") of the vector into the selected host cell may be accomplished using calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., above.

The host cells containing the vector may be cultured using standard media well known to the skilled artisan. The media will usually contain all of the nutrients necessary for the growth and survival of the cells. Suitable media for culturing *E. coli* cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate and/or fetal calf serum as necessary.

Typically, an antibiotic or other compound useful for selective growth of the transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the polypeptide has been designed to be secreted from the host cells, the majority of polypeptide will likely be found in the cell culture medium. If, however, the polypeptide is not secreted, it will be present in the cytoplasm (for eukaryotic, Gram-positive bacteria, and insect host cells) or in the periplasm (for Gram-negative bacteria host cells).

For intracellular polypeptide, the host cells are typically first disrupted mechanically or osmotically to release the cytoplasmic contents into a buffered solution. The polypeptide is then isolated from this solution. Purification of the polypeptide from solution can thereafter be accomplished using a variety of techniques. If the polypeptide has been synthesized such that it contains a tag such as Hexahistidine or other small peptide at either its carboxyl or amino terminus, it may be purified in a one-step process by passing the solution through an affinity column where the column matrix has a high affinity for the tag or for the polypeptide directly (i.e., a monoclonal antibody). For example, polyhistidine binds with great affinity and specificity to nickel, thus an affinity column of nickel (such as the Qiagen nickel columns) can be used for purification. (See, for example, Ausubel et al., eds., Current Protocols in Molecular Biology, John Wiley & Sons, New York, 1994).

Where, on the other hand, the polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the polypeptide will be found primarily in the periplasmic space of the bacteria or the cytoplasm of eukaryotic cells, the contents of the periplasm or cytoplasm, including inclusion bodies (e.g., Gram-negative bacteria) if the processed polypeptide has formed such complexes, can be extracted from the host cell using any standard technique known to the skilled artisan. For example, the host cells can be lysed to release the contents of the periplasm by the use of a French press, homogenization, and/or sonication. The homogenate can then be centrifuged.

In addition to preparing the polypeptide analogs of this invention by recombinant DNA techniques, the polypeptides may be prepared by chemical synthesis methods (such as solid phase peptide synthesis) using techniques known in the art, including those set forth by Merrifield et al. in J. Am. Chem. Soc., Volume 85, page 2149 (1964), by Houghten et al. in Proc. Natl. Acad. Sci. USA, Volume 82, page 5132 (1985), and by Stewart and Young in Solid Phase Peptide Synthesis, Pierce Chem. Co, Rockford, Ill. (1984). Chemically synthesized polypeptides may be oxidized using methods set forth in these references to form disulfide bridges.

The pI and charge of the protein analogs resulting from any of the aforementioned methods can be measured using standard techniques, such as those described further below in conjunction with the specific embodiments.

Chemically modified polypeptide compositions (i.e., "derivatives") where the polypeptide is linked to a polymer in order to modify properties are included within the scope of the present invention. The polymer is typically water soluble so that the protein to which it is attached does not precipitate in an aqueous environment, such as a physiological environment. The polymer may have a single reactive group, such as an active ester for acylation or an aldehyde for alkylation, so that the degree of polymerization may be controlled. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

In general, the polypeptide analogs of this invention will be useful for the same purposes for which the wild type proteins from which they are derived are known to be useful. For instance, NT-3 is currently under clinical study for the treatment of peripheral (including diabetic) neuropathies, while BDNF is under clinical study for the treatment of amyotrophic lateral sclerosis (ALS) . KGF is known to be active as a tissue growth and repair factor, and is currently in human clinical development for the treatment of chemotherapy- or radiation-induced mucositis. MGDF (in the form of a pegylated derivative) is in clinical development for the stimulation of platelet production as an adjunct to chemotherapy-induced thrombocytopenia. However, it is expected that the analogs of this invention will offer advantages over the unmodified forms from the standpoint of enhanced therapeutic half life and absorbability.

For therapeutic purposes, the analog polypeptides of this invention will typically be formulated into suitable pharmaceutical compositions adapted for therapeutic delivery, which constitutes an additional aspect of this invention. Such pharmaceutical compositions will typically comprise a therapeutically active amount of an analog polypeptide, alone or together with one or more excipients, carriers, or other standard ingredients for a pharmaceutical composition. The carrier material may be water for injection, preferably supplemented with other materials common in solutions for administration to mammals. Typically, the analog polypeptide will be administered in the form of a composition comprising a purified form of the polypeptide (which may be chemically modified) in conjunction with one or more physiologically acceptable carriers, excipients, or diluents. Neutral buffered saline or saline mixed with serum albumin are exemplary appropriate carriers. Other standard carriers, diluents, and excipients may be included as desired.

The pharmaceutical compositions of this invention may be prepared for storage by mixing the selected composition having the desired degree of purity with optional physiologically acceptable carriers, excipients, or stabilizers (Remington's Pharmaceutical Sciences, 18th edition, A. R. Gennaro, ed., Mack Publishing Company, 1990) in the form of a lyophilized cake or an aqueous solution. Acceptable carriers, excipients or stabilizers are nontoxic to recipients and are preferably inert at the dosages and concentrations employed, and include buffers such as phosphate, citrate, acetate, succinate or other organic acid salts; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Any composition of this invention which is intended to be used for in vivo administration must be sterile. Sterilization is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

The amount of polypeptide that will be effective in the treatment of a particular disorder or condition will depend on the nature of the polypeptide and disorder or condition, as well as the age and general health of the recipient, and can be determined by standard clinical procedures. Where possible, it will be desirable to determine the dose-response curve of the pharmaceutical composition first in vitro, as in bioassay systems, and then in useful animal model systems in vivo prior to testing in humans. In general, suitable in vivo amounts can be developed based on a knowledge of the therapeutically effective doses known for the wild type protein on which the analogs are based. The skilled practitioner, considering the therapeutic context, type of disorder under treatment, etc., will be able to ascertain proper dosing without undue effort.

Methods of introduction for administration purposes include intradermal, intramuscular, intraperitoneal, intravenous, and subcutaneous. In addition, the invention also encompasses pharmaceutical compositions comprising the polypeptide analogs administered via liposomes, microparticles or- microcapsules, which may be particularly useful to achieve sustained release.

Special delivery devices may needed in the case of some of the polypeptide analogs, such as those of NT-3, BDNF and other neurotrophic factors intended for the treatment of neurological conditions associated with the brain and other areas of the central nervous system. Such devices may include implants and osmotic pumps for intrathecal and intracranial delivery, for instance.

The analogs of this invention can also be used in accordance with standard procedures to generate antibodies that are useful for medically related purposes, such as for the monitoring of blood levels of the corresponding analog in a subject undergoing therapeutic treatment. Various procedures known in the art can be employed for the production of polyclonal antibodies that recognize epitopes of the polypeptides. For the production of antibody, various host animals can be immunized by injection with an analog polypeptide, or fragment or derivative thereof, including but not limited to rabbits, mice, rats, etc. Various adjuvants may be used to increase the immunological response, depending on the host species, including but not limited to Freund's, mineral gels such as aluminum hydroxide (alum), surface active substances such as lysolecithin, luronic polyols, polyanions, peptides, oil emulsions, eyhole limpet hemocyanins, dinitrophenol, and potentially useful human adjuvants such as Bacille Calmette-Guerin and *Corynebacterium parvum*.

For the preparation of monoclonal antibodies directed toward the analog polypeptides, any technique which provides for the production of antibody molecules by continuous cell lines in culture may be used. For example, the hybridoma technique originally developed by Kohler and Milstein and described in Nature, Volume 256, pages 495–497 (1975), as well as the trioma technique, the human B-cell hybridoma technique described by Kozbor et al in Immunology Today, Volume 4, page 72 (1983), and the EBV-hybridoma technique to produce monoclonal antibodies described by Cole et al in "Monoclonal Antibodies and Cancer Therapy", Alan R. Liss, Inc., pages 77–96 (1985), are all useful for preparation of monoclonal antibodies.

In addition, a molecular clone of an antibody to an epitope or epitopes of the polypeptide can be prepared with known techniques. In particular, recombinant DNA methodology may be used to construct nucleic acid sequences which encode a monoclonal antibody molecule or antigen-binding region thereof; see, for example, Maniatis et al., Molecular Cloning, A Laboratory Manual, Cold Spring Harbor Laboratory, Cold Spring Harbor, N.Y. (1982).

The antibodies are useful for both in vivo and in vitro diagnostic purposes, particularly in labeled form to detect the presence of the polypeptides in a fluid or tissue sample.

DESCRIPTION OF SPECIFIC EMBODIMENTS

The invention is described in further detail with reference to the following materials, methods, procedures and test results. Amino acid residues of proteins are identified the in conventional manner using the established three letter designations (for example, "met" for methionine, "val" for valine, etc.) or in some cases the established single letter designations (for example, "M" for methionine, "R" for arginine, etc.) throughout the text.

Materials and Methods

Preparation of NT-3 analogs. Amino acid residues for substitution in the native sequence of human NT-3 were selected with the aim of preserving the core structure and biological/therapeutic activity (see Holland et al., J. Mol. Biol., Volume 239, pages 385–400, 1994; Ibanez et al., in Cell, Volume 69, pages 329–341, 1992 and also in EMBO Journal, Volume 12, pages 2281–2293, 1993). The actual substitutions that were made in the native sequence of human NT-3 are reflected in the sequences shown in FIGS. 2 and 3, respectively. In one analog, shown in FIG. 2, the following two substitutions were made: arginine at position 61 ($arg_{61}$) was replaced by alanine (ala), and lysine at position 64 ($lys_{64}$) was replaced by aspartic acid (asp). This analog was designated "NT-$3_{(1-119)}$ R61A,K64D". A second analog, shown in FIG. 3, had these same two amino acid substitutions and, in addition, was truncated at residue 117 (thus deleting $arg_{118}$ and $thr_{119}$). This analog was designated "NT-$3_{(1-117)}$ R61A,K64D". To create these analogs, the mutations were introduced in the sequence of human NT-3 by standard Polymerase Chain Reaction (PCR) technology. For NT-$3_{(1-119)}$R61A,K64D, chemically synthesized oligonucleotides were used in pairs to create fragments of the NT-3 gene comprising the front portion up to the site of the mutations at the codons corresponding to positions 61 and 64 and the back portion of the gene from the mutant codons to the end. A second PCR was carried out combining the front and back portions to create the full length nucleic acid molecule encoding the two mutations at positions 61 and 64, respectively. For NT-$3_{(1-117)}$R61A,K64D, the foregoing procedure was repeated, except the back portion omitted the codons for arginine and threonine at positions 118 and 119.

Expression in *E. coli*. To express the analogs in *E. col*, a DNA sequence encoding for a methionine residue was included at the 5' end and a stop codon was placed at the 3' end in each case. In addition, cutting sites for the restriction enzymes XbaI and HindIII were placed at the extreme 5' and 3' ends of the gene, respectively, and a synthetic ribosome binding site was placed an appropriate distance upstream of the initiating methionine. The resulting synthetic gene fragments, flanked by XbaI and HindIII restriction sites at the 5' and 3' ends, respectively, contained a ribosome binding site, the ATG start codon (encoding methionine), the sequence encoding the analog, and a stop codon. The fragments were digested with restriction endonucleases NdeI and BamHI, and then ligated into the vector pAMG12.

The expression plasmid pAMG12 can be derived from the plasmid pCFM1656 (ATCC Accession No. 69576, deposited Feb. 24, 1994) by making a series of site directed base changes by PCR overlapping oligo mutagenesis and DNA sequence substitutions. Starting with the BglII site (plasmid base pair no. 180) immediately 5' to the plasmid replication promoter $P_{copB}$ and proceeding toward the plasmid replication genes, the base pair (bp) changes are as follows:

| pAMG12 bp no. | bp in pCFM1656 pAMG12 | bp changed to in |
|---|---|---|
| # 204 | T/A | C/G |
| # 428 | A/T | G/C |
| # 509 | G/C | A/T |
| # 617 | — | insert two G/C bp |
| # 679 | G/C | T/A |
| # 980 | T/A | C/G |
| # 994 | G/C | A/T |
| # 1004 | A/T | C/G |
| # 1007 | C/G | T/A |
| # 1028 | A/T | T/A |
| # 1047 | C/G | T/A |
| # 1178 | G/C | T/A |
| # 1466 | G/C | T/A |
| # 2028 | G/C | bp deletion |
| # 2187 | C/G | T/A |
| # 2480 | A/T | T/A |

-continued

| pAMG12 bp no. | bp in pCFM1656 pAMG12 | bp changed to in |
|---|---|---|
| # 2499-2502 | AGTG<br>TCAC | GTCA<br>CAGT |
| # 2642 | TCCGAGC<br>AGGCTCG | bp deletion |
| # 3435 | G/C | A/T |
| # 3446 | G/C | A/T |
| # 3643 | A/T | T/A |

In addition, the DNA sequence between the unique AatII (position #4364 in pCFM1656) and SacII (position #4585 in pCFM1656) restriction sites is substituted with the following DNA sequence (top strand SEQ ID NO: 11, lower strand SEQ ID NO: 12):

```
[AatII sticky end]

5'      CGTAACGTATGCATGGTCTCCCCATGCGAGAGTAGGGAACTGCCAGGCATCAA-
3' GCACGCATTGCATACGTACCAGAGGGGTACGCTCTCATCCCTTGACGGTCCGTAGTT-

-TAAAACGAAAGGCTCAGTCGAAAGACTGGGCCTTTCGTTTTATCTGTTGTTTGTCGGTG-

-ATTTTGCTTTCCGAGTCAGCTTTCTGACCCGGAAAGCAAAATAGACAACAAACAGCCAC-

-ACGCTCTCCTGAGTACGACAAATCCGCCGGGAGCGGATTTGAACGTTGCGAAGCAACGG-

-TGCGAGAGGACTCATCCTGTTTAGGCGGCCCTCGCCTAAACTTGCAACGCTTCGTTGCC-

-CCGGAGGGTGGCGGGCAGGACGCCCGCCATAAACTGCCAGGCATCAAATTAAGCAGAAG-

-GGCCTCCCACCGCCCGTCCTGCGGGCGGTATTTGACGGTCCGTAGTTTAATTCGTCTTC-

-CCATCCTGACGGATGGCCTTTTTGCGTTTCTACAAACTCTTTTGTTTATTTTTCTAAAT-

-CGGTAGGACTGCCTACCGGAAAAACGCAAAGATGTTTGAGAAAACAAATAAAAAGATTTA-

AatII
-ACATTCAAATATGGACGTCTCATAATTTTTAAAAAATTCATTTGACAAATGCTAAAATTC-

-TGTAAGTTTATACCTGCAGAGTATTAAAAATTTTTTAAGTAAACTGTTTACGATTTTAAG-

-TTGATTAATATTCTCAATTGTGAGCGCTCACAATTTATCGATTTGATTCTAGATTTGAGT-

-AACTAATTATAAGAGTTAACACTCGCGAGTGTTAAATACCTAAACTAAGATCTAAACTCA-

-TTTAACTTTTAGAAGGAGGAATAACATATGGTTAACGCGTTGGAATTCGAGCTCACTAGT-

-AAATTGAAAATCTTCCTCCTTATTGTATACCAATTGCGCAACCTTAAGCTCGAGTGATCA-

SacII
-GTCGACCTGCAGGGTACCATGGAAGCTTACTCGAGGATCCGCGGAAAGAAGAAGAAGAAG-

-CAGCTGGACGTCCCATGGTACCTTCGAATGAGCTCCTAGGCGCCTTTCTTCTTCTTCTTC-

-AAGAAAGCCCGAAAGGAAGCTGAGTTGGCTGCTGCCACCGCTGAGCAATAACTAGCATAA-

-TTCTTTCGGGCTTTCCTTCGACTCAACCGACGACGGTGGCGACTCGTTATTGATCGTATT-

-CCCCTTGGGGCCTCTAAACGGGTCTTGAGGGGTTTTTTGCTGAAAGGAGGAACCGCTCTT-

-GGGGAACCCCGGAGATTTGCCCAGAACTCCCCAAAAAACGACTTTCCTCCTTGGCGAGAA-

-CACGCTCTTCACGC 3'

-GTGCGAGAAGTG      5'

[SacII sticky end]
```

The ligation product was transformed into competent host cells of E. coli strain FM15. Resulting colonies were screened for the production of recombinant protein and those colonies producing the correct-sized protein were verified by DNA sequencing. The correct strain was inoculated for fermentation by transferring a small amount to Luria Broth (10 g/l of Trypticase-Peptone, 10 g/l of Yeast Extract, and 5 g/l of sodium chloride) and incubating at 30° C. for sixteen hours with stirring at 250 rpm. The culture was transferred to sterile medium that had been sterilized in place in a fermentor, then the mass of the cells was increased using continuous feeds of glucose and organic nitrogen, before being induced with lactose. After induction, the fermentation was halted, the cells were harvested by centrifugation, the supernatant was removed, and the remaining cell paste was frozen.

Protein purification. Cells from the paste were broken by high pressure homogenization and inclusion bodies were recovered by centrifugation. The inclusion bodies were solubilized in guanidine-HCl, then diluted into urea. After standing for several days, the solution was adjusted to pH 3, diluted with water, centrifuged, and eluted in series through cation exchange and hydrophobic interaction chromatography columns. The peak fractions were pooled and sterile filtered.

Isoelectric Point and protein charge. The isoelectric points of wild type human NT-3 (r-metHuNT-3, SEQ ID NO: 1), and of the analogs thereof (i.e., SEQ ID NOS: 3 and 5) were calculated using the "GCG" protein/DNA Sequence Analysis Software Package available from Genetics Computer Group, Inc., Madison, Wis. The charge of the molecule at physiological pH (assumed to be pH 7.4) was estimated using the same software. The pI of the first analog, NT-3$_{(1-119)}$R61A,K64D (SEQ ID NO: 3), was calculated to be about 0.9 pH units below that of wild type NT-3 (8.5, compared to 9.4). The charge at physiologic pH (7.4) for this analog represented a reduction of about 2.5 pH units from that of wild type NT-3 (i.e., from approximately +7 to +4.5). The pI for the other analog, NT-3$_{(1-117)}$R61A,K64D (SEQ ID NO: 5) was calculated to be approximately 8.2, which was about 1.2 pH units lower than the pI of wild type NT-3 (9.4). Moreover, the charge at physiologic pH for this analog was decreased by approximately 3.5 pH units, to about +3.5, relative to wild type NT-3 (+7).

ELISA Assay. The ELISA assay was conducted on 96-well plates coated with a monoclonal antibody raised against human NT-3. A rabbit polyclonal antibody conjugated to horse radish peroxidase was used as the secondary antibody. Serum samples, calibration standards, and quality control samples were diluted with phosphate buffer to a 50% serum matrix before assay. The sample size was 100 microliters ($\mu$l) per well. Each sample was assayed in duplicate. The limits of quantification were 0.65, 4.00, and 4.05 ng/ml of serum for wild type NT-3, NT-3$_{(1-119)}$R61A,K64D and NT-3$_{(1-117)}$R61A,K64D, respectively.

Size Exclusion Chromatography (SEC-HPLC). Size exclusion chromatography on each sample was performed using a Waters 600 system in conjunction with a G2000SWXL column (TosoHaas). Samples were eluted at a flow rate of 0.7 milliliters per minute (ml/min) in a buffer consisting of 100 mM sodium phosphate, 0.5 M NaCl, pH 6.09. Peaks were detected at a wavelength of 230 nanometers (nm).

Cation Exchange Chromatography (CEX-HPLC). CEX-HPLC was performed using a Waters 625 system with a Resource S column (Pharmacia, Uppsala, Sweden). Samples were eluted at a flow rate of one milliliter per minute using a sodium chloride gradient from 0–1 M in 20 mM Tris HCl, pH 8.5. Peaks were detected using a wavelength of 220 nm.

Silver Stained SDS-PAGE. Proteins were diluted with 2% SDS, mixed with sample buffer, and heated for five minutes in boiling water. The separation was conducted according to manufacturer's instructions using precast TRIS-Tricine gradient gels, 10–20%, from ISS (Integrated Separations Systems, Natick, Mass.). Silver staining was done according to the procedure of Blum et al. in Electrophoresis, Volume 8, pages 93–99 (1987).

Mitogenic Bioassay With 3T3trkC Cells. The biological activity of r-metHuNT-3 as a reference standard is determined by means of a cell mitogenic bioassay utilizing 3T3trkC cells. These cells are created by transfecting 3T3 cells (ATCC), which normally do not express trkC receptor on their surface, with plasmid pcDNA1/neo (Invitrogen, San Diego, Calif.) modified to contain the DNA sequence for human trkC receptor protein. See Shelton et al., Journal of Neuroscience, Volume 15, pages 477–491 (1995) for the sequence of the trkC gene, and Valenzuela et al., Neuron, Volume 10, pages 963–974 (1993) for an illustrative transfection procedure. The transfected cells are maintained at 37±2° C., in a high humidity incubator under an atmosphere containing 5.5±1.0% $CO_2$ and in Dulbecco's Minimum Essential Medium with fetal bovine serum and G-418 Sulfate. The cells are distributed into 96-well plates for each assay. After approximately twenty four hours of incubation time under the same conditions, the maintenance medium is replaced with RPMI 1640 and test samples are added. Varying concentrations of a standard and a test sample of r-metHuNT-3 are prepared in RPMI 1640 and added to the appropriate wells. The plates are returned to the incubator for approximately twenty four hours, then the cells are stained for viability with 3-(4,5-dimethylthiazol-2-yl)-5-(3-carboxymethoxyphenyl)-2-(4-sulfophenyl)2H-tetrazolium salt (MTS), a tetrazolium compound. The plates are returned to the incubator for approximately five hours, after which the optical density of each well is read at 490 nm. A dose-response standard curve is constructed and a linear regression analysis is performed on the linear portion of the standard curve. The concentration of test sample dilutions falling within the linear extracted range of the standard curve are then determined.

In Vivo Bioloical Testina. The effect of amino acid changes on the biological properties of a molecule was evaluated in vivo in male Sprague Dawley rats, using a "cross-over" test design. In particular, nine animals were divided into three groups of three rats each, and the rats were administered wild type NT-3, NT-3$_{(1-119)}$ R61A,K64D, or NT-3$_{(1-117)}$ R61A,K64D at a dose of 1 milligram per kilogram of body weight (mg/kg) each. The test material was administered either (1) intravenously (IV) as a first dose, then subcutaneously (SC) at twenty four hours after the first dose, or (2) in the reverse manner. Serial blood samples were collected before dosing and at 1, 5, 15, and 30 minutes, and 1, 2, 4, and 8 hours after an IV dose. Following subcutaneous dosing, samples were collected at 10 and 30 minutes, and at 1, 2, 4, and 8 hours. Blood serum concentrations of NT-3 were determined using an ELISA assay (see above). The antibodies used in the assays were specific for quantitation of wild type NT-3. Though not fully optimized, the antibodies displayed sufficient cross-reactivity with NT-3$_{(1-119)}$ R61A,K64D and NT-3$_{(1-117)}$ R61A,K64D to allow for quantitation of these analogs also. Standard curves were prepared for each protein (see FIG. 4).

Test Results

Characterization of NT-3 analogs. Both of the analogs, NT-3$_{(1-119)}$R61A,K64D and NT-3$_{(1-117)}$ R61A,K64D, were seen to retain the activity of wild-type NT-3 (r-metHuNT-3)

in the PC-12 in vitro bioassay (Table 1). In fact, the bioactivity of the analogs as evaluated in this assay appeared to be somewhat greater than that of wild-type NT-3, perhaps indicating an increased affinity for the trlC (NT-3) receptor.

TABLE 1

In Vitro Bioactivity of NT-3 Proteins

| NT-3 Anatog | Concentration submitted (mg/ml) | Measured concentration (mg/ml) | Percentage of expected activity (%) |
|---|---|---|---|
| Wild-type NT-3 | 0.32 | 0.23 | 72 |
| NT-3$_{(1-117)}$ R61A, K64D | 0.36 | 1.18 | 328 |
| NT-3$_{(1-119)}$ R61A, K64D | 0.25 | 1.31 | 524 |

Figure 5:
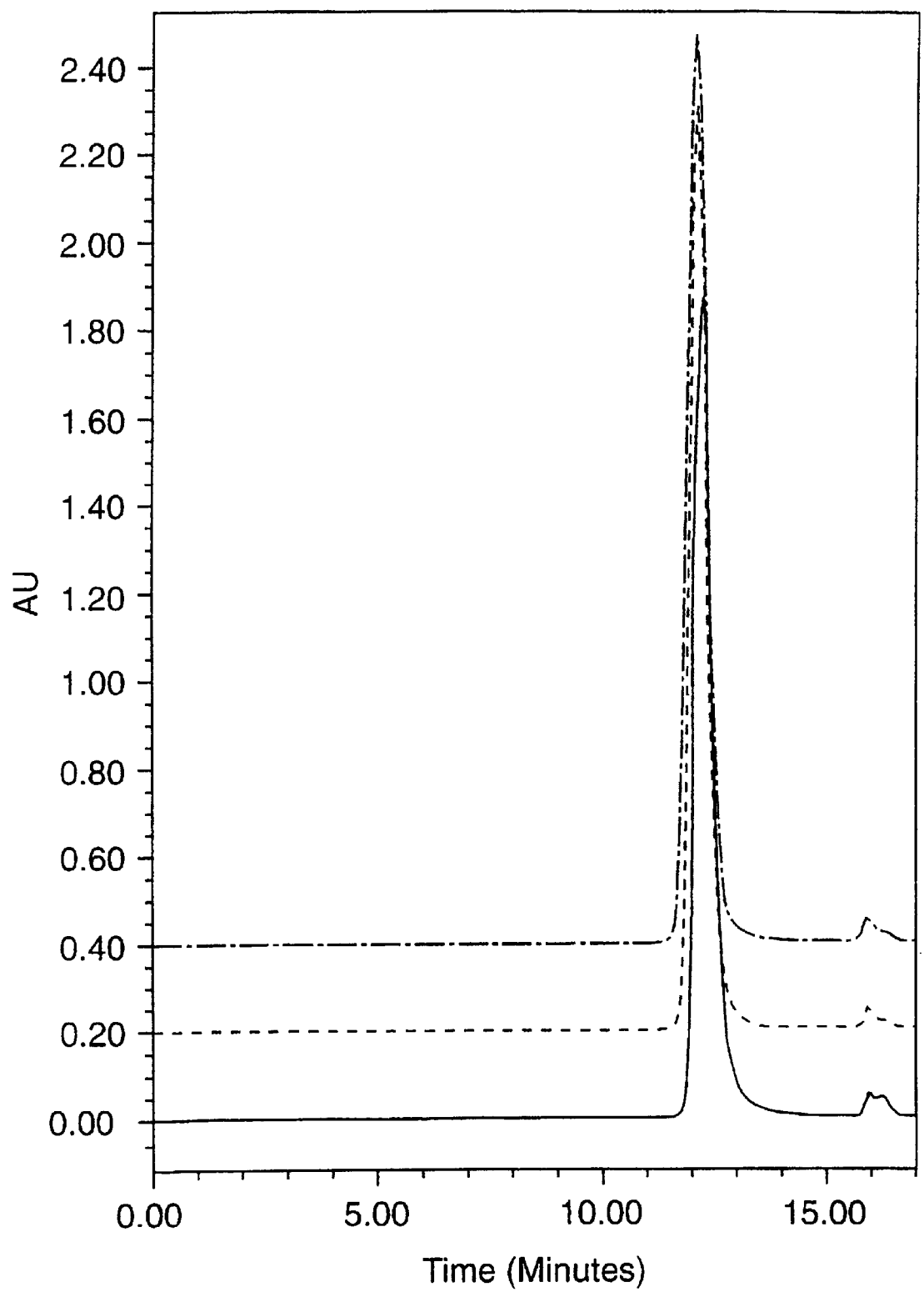

Both analogs eluted as noncovalent dimers on size exclusion-HPLC, the same as for wild type NT-3 (see FIG. 5). As expected, there was no significant difference in the molecular weights of the three proteins. No significant protein aggregation was detected for either analog. The results of cation exchange-HPLC (see FIG. 6) were consistent with aL reduction in pI for both analogs. The change in protein charge probably accounts for slight shifts in the SDS-PAGE (FIG. 7), compared to wild type NT-3. Both of the analogs retain the biological activity and noncovalent dimer structure of wild type NT-3.

Pharmacokinetic Behavior. Serum concentration curves following intravenous administration were seen to be binhasic (see FIG. 8). There was a significant difference in the initial distribution phase among the various NT-3 types. The half lites ($\alpha T_{1/2}$) were 3.3, 5.4 and 7.6 minutes for wild type NT-3, NT-3$_{(1-119)}$R61A,K64D, and NT-3$_{(1-117)}$ R61A,K64D, respectively (see Table 2, below). The observed decrease in clearance following intravenous administration could be due solely to the slower distribution of the NT-3 analogs. The most pronounced decrease in concentration during this phase was observed with wild type NT-3. The terminal phase half lives ($\beta T_{1/2}$) were similar for the three types and ranged from 0.9 to 1.0 hours, suggesting that the elimination mechanism for these types could be the same. The areas under the concentration-time curves (t-AUCinf) for NT-3$_{(1-117)}$ R61A,K64D and NT-3$_{(1-119)}$R61A,K64D were approximately 1.2 to 2-fold that of wild type NT-3.

TABLE 2

Pharmacokinetic Parameters Obtained in Rats Given a Single IV Dose of 1 mg/kg of NT-3 Proteins

| NT-3 Type | t-AUC(inf)[1] (ng-hr/ml) | CL[2] (ml/kg-hr) | $\alpha T_{1/2}$[3] (min) | $\beta T_{1/2}$[4] (hr) |
|---|---|---|---|---|
| Wild type | 724.1± 151.0 | 1411.7± 294.4 | 3.3± 0.3 | 1.0± 0.6 |
| NT-3$_{(1-119)}$ R61A, K64D | 880.7± 320.3 | 1276.2± 581.8 | 5.4± 1.9 | 0.9± 0.6 |
| NT-3$_{(1-117)}$ R61A, K64D | 1420.7± 117.9 | 706.3± 58.7 | 7.6± 0.0 | 1.0± 0.0 |

[1]Area under the serum concentration time curve from time zero to infinity. Area calculation is by trapezoidal method.
[2]Clearance rate is calculated by: Dose ÷ AUC.
[3]Distribution phase half life ($\alpha T_{1/2}$).
[4]Terminal phase half life ($\beta T_{1/2}$).

Following subcutaneous injection, the serum concentration increases rapidly for wild type NT-3 (see FIG. 9). The time to maximum concentration ($T_{MAX}$) was approximately 0.17 hour (see Table 3, below). A slower absorption profile was observed for the modified types. Specifically, $T_{MAX}$'s for NT-3$_{(1-119)}$ R61A,K64D and NT-3$_{(1-117)}$R61A,K64D were 0.67 and 1.33 hours, respectively. The maximum concentrations for NT-3$_{(1-119)}$ R61A,K64D and NT-3$_{(1-117)}$ R61A,K64D were 6 to 10 times higher than for wild type NT-3, suggesting that the analogs manifested a greater degree of absorption from the site of injection following administration. Furthermore, the degree or extent of absorption (bioavailability) is more typically determined from the ratio of the areas under the serum curves for subcutaneous and intravenous routes of administration, Table 3. The bioavailability for wild type NT-3, NT-3$_{(1-119)}$ R61A,K64D, and NT-3$_{(1-117)}$R61A,K64D was 2.2, 28.5 and 43.22%, respectively. The terminal half lifes for the analogs appear to be longer than that of the wild type.

TABLE 3

Pharmacokinetic Parameters Obtained in Rats Given a Single SC Dose of 1 mg/kg of NT-3 Proteins

| NT-3 Type | t-AUC(inf)[1] (ng-hr/ml) | F[2] (%) | CMAX[3] (ng/ml) | TMAX[4] (hr) | $\beta T_{1/2}$[5] (hr) |
|---|---|---|---|---|---|
| Wild type | 15.2± 9.5 | 2.2± 1.3 | 17.8± 11.6 | 0.2± 0.0 | 0.4± 0.0 |
| NT-3$_{(1-119)}$ R61A, K64D | 241.3± 74.8 | 28.5± 6.3 | 106.5± 47.1 | 0.7± 0.3 | 1.4± 0.6 |
| NT-3$_{(1-117)}$ R61A, K64D | 632.9± 38.0 | 43.2± 2.0 | 180.1± 51.2 | 1.3± 0.6 | 1.4± 0.8 |

[1]Area under the serum concentration time curve from time zero to infinity. Area calculation is by trapezoidal method.
[2]Bioavailability (F) is calculated by: (t-AUC$_{SC}$ ÷ t-AUC$_{IV}$) × 100%, where both areas were obtained from the same animal.
[3]CMAX is the maximal concentration.
[4]TMAX is the time to maximal concentration.
[5]Terminal phase half life ($\beta T_{1/2}$).

The results from these studies show that by decreasing the pI of NT-3, one can lower the clearance rate following intravenous administration, at least initially, and also enhance the extent of absorption following subcutaneous administration. These results also demonstrate that the charge of the protein plays a significant role in determining pharmacokinetic behavior. In the case of a basic protein such as NT-3, as well as other cationic proteins, decreasing the isoelectric point (or the charge at physiological pH) can lead to significant improvement in the absorption and bioavailability of the molecule following subcutaneous administration. From this knowledge, and the description provided herein, it is possible to design new molecules of improved therapeutic value.

It should be noted that the analogs illustrated in the foregoing description are intended to be exemplary only, and that additional analogs of NT-3, as well as of other proteins, can be created in light of the present description to achieve lower isolectric points with longer circulation times and/or higher absorption. In one variation, for instance, the particular analog proteins of SEQ ID NOS: 3 and 5 can be produced by expressed in a mammalian cell or a secreting bacterial strain such that a "met-less" product is obtained (i.e., the methionine residue at the N-terminus is processed away, to result in the polypepcides of SEQ ID NOS: 6 and 7, respectively, as will be true in the case of the BDNF analogs described below).

BDNF Analogs

Using the procedures described above for NT-3, the following analogs of BDNF were prepared and purified from *E.coli* and the isoelectric point (pI) and (approximate) net charge at physiological pH (7.4) were measured for each.

The pI and charge at physiological pH for "wild type" BDNF (i.e., of naturally occurring sequence; see U.S. Pat. No. 5,180,820, FIG. 5) (SEQ ID NO: 8) are also shown for purposes of comparison. Positions for substitution are numbered beginning with the first residue following methionine in the mature form of the protein as expressed in *E. coli*. (i.e., the initial methionine residue is not counted).

BDNF, K65D, K73D, K95A, R97A

Substitutions were lysine to aspartic acid at positions 65 and 73, lysine to alanine at position 95, and arginine to alanine at position 97 (SEQ ID NO: 9).

Calculated pI: 8.46

Charge: +4.0

BDNF, P60E, K65D, K73D, K95A

Substitutions were proline to glutamic acid at position 60, lysine to aspartic acid at positions 65 and 73, and lysine to alanine at position 95 (SEQ ID NO: 10).

Calculated pI: 8.45

Charge: +4.0

Wild Type BDNF

Calculated pI: 10.23

Charge: +9.5

Biological Test Results and Characterization

1) In Vitro Bioactivity: Mitogenic Bioassay with PC12/ trkC Cells. In this assay, the biological activity of wild type BDNF and the BDNF analogs is determined quantitatively by measuring the incorporation of (MTS) into PC-12 cells (ATCC) that have been transformed to express trkB receptor (the high affinity receptor for BDNF). The transformed cells are maintained at 37±2° C., in a high humidity incubator under an atmosphere containing 7.5±1% carbon dioxide, in Dulbecco's Minimum Essential Medium containing fetal bovine serum and horse serum and 1% L-glutamine. The cells are distributed into well plates for assaying, and incubation is continued. After approximately forty eight hours, the maintenance medium is replaced with RPMI 1640 Medium, the test samples are added, and incubation is continued under the same conditions for another forty eight hours. The cells are then stained with MTS, incubated under the same conditions for another five hours, and the optical density for each well is read with a microplate reader at 490 nm. The results for bioactivity of the two BDNF analogs versus wild type BDNF are given in Table 4, below.

TABLE 4

In Vitro Bioactivity of BDNF Proteins

| | Bioactivity (mg/mg) |
|---|---|
| Wild-type BDNF | 0.61 |
| BDNF, K65D, K37D, K95A, R97A | 1.24 |
| BDNF, P60E, K65D, K73D, K95A | 0.61 |

2) In Vivo Biological Testing and Results. The biological properties of the analogs were evaluated in vivo in male Sprague Dawley rats at a dose of 3.0 milligrams per kilogram of body weight for BDNF, K65D, K73D, K95A, R97A and 1.7 milligrams per kilogram of body weight for BDNF, P60E, K65D, K73D, K95A. The test materials were administered intravenously and subcutaneously, followed by collection of blood samples and measurement of blood serum concentrations (see same procedure described above for NT-3 and NT-3 analogs).

The pharmacokinetic behavior is given below with respect to each form of administration.

TABLE 5

Pharmacokinetic Properties in Rats, Single Intravenous (IV) Dose of BDNF Proteins

| BDNF Type | t-AUC(inf) (ng-hr/ml) |
|---|---|
| Wild type | 8652.8± 833.6 |
| BDNF, K65D, K73D, K95A, R97A | 12932.8± 913.0 |
| BDNF, P60E, K65D, K73D, K95A | 14097.2± 949.8 |

TABLE 6

Pharmacokinetic Properties in Rats, Single Subcutaneous (SC) Dose of BDNF Proteins

| BDNF Type | t-AUC(inf) (ng-hr/ml) | F (%) |
|---|---|---|
| Wild type | 462.5± 130.3 | 4.7± 2.0 |
| BDNF, K65D, K73D, K95A, R97A | 2401.6± 297.1 | 16.8± 0.1 |
| BDNF, P60E, K65D, K73D, K95A | 2049.2± 357.4 | 13.9± 2.0 |

These results show that the introduction of the mutations into wild type BDNF has a measurable effect on pharmacokinetic properties. In particular, greater in vivo bioavailability is achieved for the two BDNF analogs in comparison with wild type BDNF as reflected by the increased values for t-AUC(inf) following intravenous administration and the increase in t-AUC(inf) and F % following subcutaneous administration.

The invention is defined in the appended claims.

What is claimed is:

1. An isolated DNA molecule which encodes the polypeptide of SEQ ID NO: 9.
2. An isolated DNA molecule which encodes the polypeptide of SEQ ID NO: 10.
3. A biologically functional expression vector which includes a DNA molecule according to claims 1 or 2 operatively linked to expression regulatory sequences.
4. A prokaryotic or eukaryotic host cell transformed or transfected with an expression vector according to claim 3 in a manner allowing the host cell to express the polypeptide encoded by the DNA molecule.
5. A transformed or transfected bacterial host cell according to claim 4.
6. A transformed or transfected *E. coli* host cell according to claim 5.
7. A transformed or transfected mammalian host cell according to claim 4.
8. A transformed or transfected CHO cell according to claim 7.
9. A transformed or transfected COS cell according to claim 7.
10. A process for the production of the polypeptide of SEQ ID NO: 9 or SEQ ID NO: 10, said process comprising culturing under suitable nutrient conditions a prokaryotic or eukaryotic host cell transformed or transfected with an expression vector comprising an isolated DNA molecule encoding said polypeptide in a manner allowing the host cell to express the polypeptide, and isolating the polypeptide product of the expression.
11. A process according to claim 10 in which the DNA molecule has been prepared by site directed mutagenesis.
12. A process according to claim 10, in which the host cell is bacterial.
13. A process according to claim 12, in which the bacterial host cell is *E. coli*.

* * * * *

UNITED STATES PATENT AND TRADEMARK OFFICE
CERTIFICATE OF CORRECTION

PATENT NO. : 6,211,150 B1
DATED : April 3, 2001
INVENTOR(S) : Boone et al.

It is certified that error appears in the above-identified patent and that said Letters Patent is hereby corrected as shown below:

<u>Column 2,</u>
Line 30, change "methicnine" to -- methionine --.

<u>Column 3,</u>
Line 59, change "w70 91/03568" to -- WO 91/03568 --.

<u>Column 4,</u>
Line 14, change "succinviation" to -- succinylation --.
Line 38, change "piasmid" to -- plasmid --.

Signed and Sealed this

Ninth Day of April, 2002

Attest:

JAMES E. ROGAN
*Director of the United States Patent and Trademark Office*

*Attesting Officer*